United States Patent [19]

Scheben et al.

[11] Patent Number: 4,499,298

[45] Date of Patent: Feb. 12, 1985

[54] PROCESS FOR THE PRODUCTION OF ESTERS

[75] Inventors: John A. Scheben, Erlanger, Ky.; James A. Hinnenkamp, Cincinnati, Ohio

[73] Assignee: National Distillers and Chemical Corporation, New York, N.Y.

[21] Appl. No.: 105,444

[22] Filed: Dec. 20, 1979

Related U.S. Application Data

[63] Continuation of Ser. No. 801,283, May 27, 1977, abandoned.

[51] Int. Cl.$^3$ .................... C07C 67/00; C07C 69/007; C07C 69/157; C07C 67/055
[52] U.S. Cl. ............................ 560/241; 260/410.5; 502/159; 502/170; 502/174; 502/184; 502/215; 502/242; 502/243; 502/245; 502/328; 502/329; 502/330; 502/331; 549/240; 560/66; 560/106; 560/107; 560/109; 560/131; 560/240; 560/254; 560/255

[58] Field of Search ............... 560/241, 106, 107, 109, 560/66, 254, 255, 240, 131; 260/410.5, 346.4; 252/430, 443, 447, 456, 472–474, 464; 549/240

[56] References Cited

U.S. PATENT DOCUMENTS 3,547,982 12/1970 McKeon et al. .................... 560/241
4,033,999 7/1977 Anoda et al. ....................... 560/241

FOREIGN PATENT DOCUMENTS 747415 11/1966 Canada ............................. 560/245
45-14528 5/1970 Japan ................................ 560/245
7009481 1/1971 Netherlands ..................... 560/245
981987 2/1965 United Kingdom .............. 560/245

*Primary Examiner*—Vivian Garner
*Attorney, Agent, or Firm*—Kenneth D. Tremain

[57] ABSTRACT

A process is described for the preparation of aryl esters such as benzyl acetate by reacting an aryl alkyl compound such as toluene with a carboxylic acid such as acetic acid and oxygen in the presence of a catalytically effective amount of a catalyst comprising palladium metal, gold metal and a metal of Group VA of the Periodic Table of the Elements such as bismuth.

8 Claims, No Drawings

PROCESS FOR THE PRODUCTION OF ESTERS

This is a continuation of application Ser. No. 801,283 filed May 27, 1977, now abandoned.

BACKGROUND OF THE INVENTION

U.S. Pat. No. 3,275,680, Great Britain Pat. No. 1,017,938 and Great Britain Pat. No. 1,117,595 each describe the preparation of benzyl acetate and other benzyl esters wherein an alkyl-substituted phenyl compound such as toluene is reacted in the gaseous phase with an oxygen containing gas, for example, air, acetic acid, and an alkali metal acetate in the presence of a catalyst containing palladium metal supported upon a suitable substrate. The reported quantities of benzyl acetate produced per gram of palladium metal are relatively low. Canadian Pat. No. 820,352 describes a similar process wherein the catalyst contains metallic palladium and gold, and an alkali metal salt such as sodium acetate. Investigation has shown that while this catalyst is much more efficacious than the aforedescribed palladium metal catalysts, there is still considerable room for improvement in process yields.

Great Britain No. 1,328,058 describes a process for preparing benzyl acetate by the reaction of toluene, oxygen and acetic acid in the gaseous phase at an elevated temperature in the presence of a supported catalyst system containing an oxide, hydroxide or carboxylate of palladium and bismuth, or in the case of palladium, the metal itself, and a hydroxide, carbonate or carboxylate of an alkali metal compound. Other metals, including gold and/or copper, or compounds of these metals which do not contain halogen, sulfur or nitrogen, may be added so as to affect the activity and selectivity of the catalyst. Illustrative of a catalyst system of Great Britain Pat. No. 1,328,058 is one containing palladium metal, bismuth acetate and potassium acetate. Use of this catalyst system in the production of benzyl acetate from toluene has provided, at best, only very modest levels of productivity.

It has now been found that toluene and other aryl alkyl compounds can be selectively catalytically oxidized to benzyl acetate and other such esters using a catalytically effective amount of a catalyst comprising palladium, gold, a metal selected from Group VA of the Periodic Table and optionally, one or more promoters. It is indeed surprising that high selectivity can be obtained using the present inventive process since attempted oxidations of toluene to benzyl acetate using known and conventional catalyst systems have provided extremely low conversions to benzyl acetate. The present process, however, provides high selectivity for production of benzyl acetate and other such esters. The yield of these esters realized by the present invention affords a process which is amenable to commercial production of benzyl acetate, a valuable chemical product and intermediate, and such esters in general.

SUMMARY OF THE INVENTION

This invention relates to the oxidation of aryl alkyl compounds to the corresponding aryl alkyl esters and, more particularly, relates to such a process utilizing a catalyst comprising palladium metal, gold metal and a metal selected from Group VA of the Periodic Table of the Elements.

The starting aryl alkyl compound for the present process is a toluene compound, i.e. toluene and substituted toluenes wherein the substituent may be lower alkyl and alkoxy, aryl, aryloxy, carboxy, carbo(lower)alkoxy, or acyl groups derived from lower alkanoic and aryl carboxylic acids. The number of substituents can range from one to five on the aromatic ring, but preferably is not greater than two. Representative compounds include toluene, xylene, cymene, mesitylene, durene, pentamethylbenzene, hexamethylbenzene, methylnaphthalene, p-phenyltoluene, 2,2-bis(p-tolyl)propane, p-phenoxytoluene, di-p-tolyl ether, 2,5-dimethoxytoluene, methyl p-toluate, p-toluic acid, p-methyl benzophenone, 4-methylphthalic anhydride, and the like.

Where the toluene starting compound contains lower alkyl substituents, especially methyl substituents, oxidation of such groups can occur. For example, the oxidation of xylene with acetic acid will yield, as the primary product, tolyl acetate (cresyl acetate) but can also result in the diacetate. Thus, oxidation of p-xylene with acetic acid will yield, as primary product p-tolyl acetate, and as secondary oxidation product, the diacetate. The preferred aryl alkyl compound for use in this process is toluene.

The starting carboxylic acid can be formic, acetic, propionic, butyric, pivalic, octanoic, benzoic, lauric, stearic, and the like. The preferred carboxylic acid for use in this process is acetic acid.

In the following description of preferred embodiments, reference is principally made to the oxidation of toluene with acetic acid, the preferred starting compounds, to benzyl acetate, but it should be understood that the process description is applicable to substituted toluenes, as hereinbefore described.

DESCRIPTION OF THE PREFERRED EMBODIMENTS

Toluene, the preferred starting aryl alkyl compound for the process herein may be used in pure form or in diluted form, such as, for example, in the form of a mixture containing up to about 50% of diluents, usually inert hydrocarbons, e.g., heptane, hexane or cyclohexane. The preferred carboxylic acid for use herein, acetic acid, is advantageously provided as glacial acetic acid.

The oxidizing agent employed can be pure oxygen or an oxygen containing gas mixture such as air or air enriched with oxygen and the gas mixture may also contain an inert diluent gas such as carbon dioxide, or nitrogen.

The amount of oxidizing agent employed is not excessively critical since the product, benzyl acetate, can be separated from the reaction product and unreacted toluene recycled. Thus, stoichiometric proportions of oxygen, i.e., one mole of oxygen per two moles of toluene, can be used. As desired, the amount of oxygen incorporated into the reaction can be from about 1 to about 99 mole percent in admixture with from about 1 to about 99 mole percent of toluene which may be in the flammability range of the mixture. In general, it is preferred to operate an oxygen-lean or rich system to avoid potential flammability. Toluene to oxygen molar ratios of from about 2:1 to 4:1 are preferred. Toluene to acetic acid molar ratios can vary from about 5:1 to 1:1, and preferably are from 1:1 to 2:1.

While this reaction can be carried out in the gaseous phase, it is preferable to conduct the reaction under liquid phase conditions since lower temperatures can be utilized and greater yields of aryl ester can be obtained.

The liquid phase reaction is carried out at elevated temperatures, preferably from about 100° to about 300° C., and most preferably from about 140° to about 175° C. Sufficient pressure is used to maintain the liquid phase at the reaction temperature and, in general, the pressure will be about 10 to 2500 psig, and preferably about 80 to 2000 psig.

The catalyst employed in the process of this invention contains palladium metal, gold metal and a metal of Group VA of the Periodic Table of the Elements, i.e., bismuth, antimony or arsenic. While any of the Group VA metals can be used herein, bismuth is preferred due effective. In general, the amount of modifier can range up to about 1000% of the supported catalyst weight but it usually is preferred to use from about 5 to about 600 weight percent.

Examples 1 to 4 herein below are illustrative of known catalyst systems for the oxidative conversion of toluene to benzyl acetate and are presented by way of comparison to Examples 5 and 6 which are illustrative of the present process and catalyst system. As used throughout this specification and claims, all parts and percentages are by weight and all temperatures in degrees Centigrade unless otherwise specified.

TABLE I

| EXAMPLE[1] | PALLADIUM METAL | GOLD METAL | BISMUTH METAL | PROMOTER | SUPPORT | REACTION TIME (hours) | PARTS OF BENZYL ACETATE PER PART PALLADIUM METAL |
|---|---|---|---|---|---|---|---|
| 1 | 1.3 | — | — | 5.0 Cu(OOCCH3)2 | Al2O3 | 1 | 0 |
| 2 | 1.3 | 0.6 | — | 5.0 Cu(OOCCH3)2 | Al2O3 | 1 | 474 |
| 3 | 1.3 | 0.6 | — | 5.0 KOOCCH3 | Al2O3 | 3 | 526 |
| 4[2] | 3.3 | 1.5 | — | 16 Bi(OOCCH3)2; 30 KOOCCH3 | SiO2 | 1 | 20 |
| 5 | 0.6 | 0.4 | 1.0 | 5.0 Cu(OOCCH3)2 | Al2O3 | 1 | 773 |
| 6 | 0.6 | 0.4 | 1.0 | 5.0 Cu(OOCCH3)2 | Al2O3 | 3 | 1,421 |

[1]Reaction conditions: 150° C.; 100 psig O2 pressure; molar ratio of acetic acid to toluene = 1.9:1.0
[2]From Example H of Great Britain 1,328,058.

to its lower toxicity. Although reference is hereinafter made to the use of bismuth in the catalyst compositions of this invention, it should be understood that the following description is equally applicable to the use of antimony and arsenic as well.

The palladium-gold-bismuth catalysts of this invention are prepared by applying solutions, preferably aqueous-based, of soluble compounds of these metals to a known and conventional catalyst carrier, for example, carbon, silica, alumina, titania, zirconia, ion exchange resin, diatomaceous earth, glass beads, and the like. Alumina is the support of choice herein.

The total amount of catalyst deposited upon the carrier can vary from about 0.1 to 20% by weight, and preferably, from about 0.5 to 6% by weight of the support.

After the metal oxides/salts have been dried on the carrier, they are reduced to the elemental state with hydrogen of other known and conventional reducing medium, such as alkaline hydrazine.

Palladium to gold weight ratio can vary from about 0.5:1 to 2:1 and the amount by weight of bismuth can be equal to, and preferably greater than, the weight of palladium, consistent with acceptable levels of productivity of benzyl acetate. Excellent productivity and selectivity were found when the metals concentration was $1.2 \times 10^{-3}$ moles palladium, $6 \times 10^{-4}$ moles of gold and $1.8 \times 10^{-3}$ moles bismuth per liter of a 1:1 volume mixture of glacial acetic acid and pure toluene.

It is advantageous to employ certain metal salts and/or oxides as promoters of the catalyst systems herein, for example, zinc acetate, lead acetate, copper acetate, the acetates of alkali and alkaline earth metals such as lithium, sodium, potassium and calcium, bismuth subcarbonate, and tellurium oxide. Mixtures of the modifiers can be employed. Copper acetate and bismuth subcarbonate are preferred modifiers.

The modifiers are added to the reaction system in any convenient manner. They may be added along with the catalyst or in the materials charge, or added separately before the materials charge. The amount of modifier can vary appreciably. As little as about 0.01% by weight, based on the supported catalyst weight, will be As established by these data, a palladium metal catalyst containing copper acetate as a promoter (Example 1), resulted in no appreciable amount of benzyl acetate. The addition of gold metal to this catalyst system (Example 2) provided an operative conversion process. Substitution of potassium acetate for copper acetate (Example 3) resulted in a slightly higher yield but only after a three-fold increase in reaction time. The catalyst system of Great Britain Pat. No. 1,328,058 (Example 4) supra, performed poorly. Example 5 which is illustrative of the invention herein resulted in a dramatic increase in benzyl acetate production over that of Example 2 for an equivalent reaction period. Similarly, Example 6 which employed a catalyst system in accordance with the instant invention resulted in a marked improvement in benzyl acetate yield over the known catalyst system of Example 3.

The following example illustrates the results obtained when no promoter is employed.

EXAMPLE 7

Using a catalyst consisting of 0.6% Pd, 0.5% Au and 1.0% Bi, without added promoter, under the following reaction conditions: 150° C.; 1100 psig air pressure, reaction time: 3 hours and 1:1 molar ratio of acetic acid to toluene, 1016 grams of benzyl acetate per gram Pd are obtained.

A control run, under identical reaction conditions, using a catalyst composed of 1.3% Pd and 0.6% Au, yields 407 grams of benzyl acetate per gram Pd.

What is claimed is:

1. A process for the preparation of benzyl esters which comprises reacting toluene with a carboxylic acid and oxygen in the liquid phase in the presence of a catalytically effective amount of a supported catalyst consisting essentially of palladium metal, gold metal and a metal of Group VA of the Periodic Table of Elements.

2. A process for the preparation of benzyl acetate which comprises reacting toluene, acetic acid and oxygen in the liquid phase in the presence of a catalytically effective amount of a supported catalyst consisting essentially of palladium metal, gold metal and a metal of Group VA of the Periodic Table of Elements.

3. The process of claim 2 wherein the Group VA metal is bismuth.

4. The process of claim 2 wherein the reaction takes place at a temperature of from about 100° C. to about 300° C. and at a pressure of from about 10 to 2500 psig.

5. The process of claim 2 wherein the palladium to gold weight ratio is from about 0.5:1 to 2:1 and the Group VA metal is present in an amount by weight equal to or greater than the weight of palladium.

6. The process of claim 2 wherein the total amount of catalyst deposited upon the support is from about 0.1 to 20% by weight of the support.

7. A process for the preparation of benzyl acetate which comprises reacting toluene, acetic acid and oxygen in the liquid phase in the presence of a catalytically effective amount of a supported catalyst consisting essentially of palladium metal, gold metal, a metal of Group VA of the Periodic Table of Elements and a promoter selected from the group consisting of zinc acetate, lead acetate, copper acetate, the acetates of alkali and alkaline earth metals, bismuth subcarbonate, tellurium oxide and mixtures thereof.

8. The process of claim 7 wherein the promoter is a member of the group consisting of copper acetate and bismuth subcarbonate and the Group VA metal is bismuth.

* * * * *